US012302841B2

(12) United States Patent
Kang et al.

(10) Patent No.: US 12,302,841 B2
(45) Date of Patent: May 20, 2025

(54) SOYBEAN VARIETY COMPRISING HIGH CONTENT OF EPICATECHIN

(71) Applicants: AMOREPACIFIC CORPORATION, Seoul (KR); SEOUL NATIONAL UNIVERSITY R&DB FOUNDATION, Seoul (KR)

(72) Inventors: Young Gyu Kang, Yongin-si (KR); Moon Young Kim, Seoul (KR); Geum Ryong Park, Seoul (KR); Seok Ha Lee, Seoul (KR); Hyun Ju Jang, Seoul (KR); Jeong Min Ha, Seoul (KR); Myoyeon Kim, Yongin-si (KR); Dong Hyun Kim, Yongin-si (KR); Nok Hyun Park, Yongin-si (KR); Yong Deog Hong, Yongin-si (KR)

(73) Assignees: AMOREPACIFIC CORPORATION, Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 583 days.

(21) Appl. No.: 17/488,024

(22) Filed: Sep. 28, 2021

(65) Prior Publication Data
US 2022/0095570 A1   Mar. 31, 2022

(30) Foreign Application Priority Data
Sep. 29, 2020   (KR) ......................... 10-2020-0127321

(51) Int. Cl.
A01H 5/10     (2018.01)
A01H 6/54     (2018.01)

(52) U.S. Cl.
CPC .............. *A01H 6/542* (2018.05); *A01H 5/10* (2013.01)

(58) Field of Classification Search
None
See application file for complete search history.

(56) References Cited

U.S. PATENT DOCUMENTS 10,716,822 B2 *   7/2020   Moon ..................... A23L 33/11

FOREIGN PATENT DOCUMENTS

| CN | 101102783 A | 1/2008 |
| CN | 107176941 A | 9/2017 |
| JP | 5097996 B2 | 12/2012 |
| KR | 10-2020-0005056 A | 1/2020 |
| KR | 10-2088468 B1 | 3/2020 |
| KR | 10-2101790 B1 | 4/2020 |

OTHER PUBLICATIONS

Junior et al. Genetic potential of common bean progenies selected for crude fiber content obtained through different breeding methods. Genet. Mol. Res. May 29, 2015;14(2):5763-74. (Year: 2015).*
Junior et al. Genetic potential of common bean progenies obtained by different breeding methods evaluated in various environments. Genet. Mol. Res. Sep. 2, 2016;15(3). (Year: 2016).*
Bae Cheon Cha et al., "Comparison of Antioxidant Activity and Composition in Glycine max Merr. And Glycine soja Siebold et Zucc.", Kor. J. Pharmacogn., 27(3): 190-195 (1996).
Jeong June Choi, "Anti-Diabetic Effects of Glycine soja Extract in Genetic Animal Model of db/db Mouse", J Korean Med Obes Res, 16(2): 101-108 (2016).
Seong Su Hong et al., "Flavonoid Constituents of Acacia catechu", J Appl Biol Chem, 58(2): 189-194 (2015).
Chiaki Ito et al., "Characterisation of proanthocyanidins from black soybeans: Isolation and characterisation of proanthocyanidin oligomers from black soybean seed coats", Food Chemistry, 141: 2507-2512 (2013).
So-Hee Lee et al., "Polyphenol Contents and Antioxidant Activities of Lentil Extracts from Different Cultivars", J Korean Soc Food Sci Nutr, 45(7): 973-979 (2016).
Jing et al., "Research Process in Nutrient Ingredient and Biological Activities of Glycine soja Seeds", Soybean Science, 2019, vol. 38, No. 4, pp. 644-649, with English abstract.
Zheng et al., "Chemical Constituents of Antioxidant Species Black Soybean", Food Science, 2014, vol. 36, No. 6, pp. 155-160, with English abstract.

* cited by examiner

*Primary Examiner* — Cynthia E Collins
(74) *Attorney, Agent, or Firm* — Merchant & Gould P.C.

(57) ABSTRACT

The present disclosure relates to a new soybean variety containing epicatechin with high content and having antioxidant and antiaging activities, a method for producing the new soybean variety, a composition containing an extract of the new soybean variety as an active ingredient, a functional health food containing the new soybean variety, a method for producing epicatechin from the new soybean variety, and a method for producing a commodity plant product. The seed of the new soybean (*Glycine max*) variety according to an aspect of the present disclosure contains epicatechin with a high content of 2 wt % or more based on the total weight of an 80 wt % ethanol aqueous solution of seed extract, exhibits 2 times or higher antioxidant activity confirmed by DPPH radical-scavenging ability than the mother plant IT109098, and exhibits superior collagenase (matrix metalloproteinase-1, MMP-1) expression inhibition as compared to EGCG, which is known as an antiaging substance.

9 Claims, 12 Drawing Sheets

FIG. 1

SOYBEAN VARIETY COMPRISING HIGH CONTENT OF EPICATECHIN

CROSS-REFERENCE TO RELATED APPLICATIONS

This application claims priority to Korean Patent Applications No. 10-2020-0127321, filed on Sep. 29, 2020, and all the benefits accruing therefrom under 35 U.S.C. § 119, the entire contents of which are hereby incorporated by reference.

TECHNICAL FIELD

The present disclosure relates to a new soybean variety which contains epicatechin with high content and has antioxidant and antiaging activities, a method for producing the new soybean variety, a composition containing an extract of the new soybean variety as an active ingredient, a functional health food containing the new soybean variety, a method for producing epicatechin from the new soybean variety and a method for producing a commodity plant product.

BACKGROUND ART

Soybean (*Glycine max*) is a crop plant native to the Northeast Asia region including Korea, which has been cultivated since before the Christian era in the Korean peninsula. It has been specialized into a variety suitable for food over thousands of years and has been used not only as food but also as folk medicine. Considering that Qimin Yaoshu (530-550 A.D.), the oldest Chinese agricultural text, describes varieties such as yellow Korean soybean, black Korean soybean, etc., it is thought that various varieties of soybean would have been cultivated in the Korean peninsula around the 4th or 5th century. It is thought that various varieties of "Korean soybean" were cultivated in China since Koguryo was called 'Korea' at that time. Wild soybean (*Glycine soja*) from which the cultivated species originate and semi-wild varieties are distributed throughout Korea, and indigenous native species not found in other countries are being cultivated in farmhouses.

With the agreement of the Nagoya Protocol on Access to Genetic Resources and the Fair and Equitable Sharing of Benefits Arising from their Utilization (ABS) at the 10th Convention on Biological Diversity (CBD) held in Nagoya in 2010, the importance of the unique biological resources of different countries is recognized anew and the discovery, development and utilization of the biological resources have become more important. In order to expand the production of Korean soybean and ensure international competitive power, the improvement of the quality of edible soybean and the development of new soybean variety are very important. Korea has comparative advantage in terms of the development of functional and special soybean varieties with various and peculiar genetic resources as the origin of soybean. The present disclosure has been made to develop a cultivar rich in antioxidant ingredients including wild soybean-derived epicatechins, etc. by artificially corssing Korean native soybean with wild soybean or semi-wild soybean for industrial utilization as natural functional ingredients of cosmetics and functional health food materials.

DISCLOSURE

Technical Problem

As inexpensive soybean is imported at low or no tariff with the advent of the WTO system in 1990s and surging international FTA agreements, the Korean soybean industry has lost competitive edge and is shrinking greatly. The present disclosure has been made to develop anew functional variety distinguished from imported soybean for utilization of Korean soybean in functional cosmetics and food industries.

The inventors have selected from among wild soybean (*Glycine soja*) and semi-wild soybean resources growing naturally in Korea those having high epicatechin content and high antioxidant activity and generated new species through corssing with cultivated soybean. Then, elite lines were selected and characters were fixed according to a breeding program. From the selected elite lines, a new soybean variety containing epicatechin at high content and having superior antioxidant and antiaging activities according to an aspect of the present disclosure was developed by evaluating crop characteristics, epicatechin content, antioxidant activity (DPPH radical-scavenging ability), skin antiaging effect (collagenase expression-inhibiting ability), etc.

In an aspect, the present disclosure is directed to providing a new soybean variety containing epicatechin with high content. In another aspect, the present disclosure is directed to providing a new soybean variety having antioxidant or antiaging activity.

In another aspect, the present disclosure is directed to providing a method for producing a new soybean variety.

In another aspect, the present disclosure is directed to providing an antiaging composition containing an extract of the new soybean variety as an active ingredient.

In another aspect, the present disclosure is directed to providing an antioxidant composition containing an extract of the new soybean variety as an active ingredient.

In another aspect, the present disclosure is directed to providing a functional health food containing the new soybean variety.

In another aspect, the present disclosure is directed to providing a method for producing epicatechin from the new soybean variety.

In another aspect, the present disclosure is directed to providing a method for producing a commodity plant product from the new soybean variety.

Technical Solution

In an aspect, the present disclosure provides a new soybean (*Glycine max*) variety, wherein the new soybean variety is obtained by corssing IT109098 (a local collection, Naptegikong) as a mother plant with semi-wild K7-2 as a father plant, and the new soybean variety has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits IC % of 70 ppm or lower in antioxidant activity test through DPPH reduction; and (3) the extract of the new soybean variety exhibits collagenase expression inhibition of 60% or higher in collagenase expression inhibition test.

In another aspect, the present disclosure provides a method for producing a new soybean variety, which includes: corssing a soybean plant; and harvesting a soybean seed obtained from the corssing, wherein one or more of the soybean plant is the new soybean variety described above.

In another aspect, the present disclosure provides an antiaging composition containing an extract of the new soybean variety as an active ingredient.

In another aspect, the present disclosure provides an antioxidant composition containing an extract of the new soybean variety as an active ingredient.

In another aspect, the present disclosure provides a functional health food containing the new soybean variety in another aspect, the present disclosure provides a method for producing epicatechin, which includes extracting epicatechin from the new soybean variety.

In another aspect, the present disclosure provides a method for producing a commodity plant product, which includes: obtaining the new soybean variety; and producing a commodity plant product containing a protein concentrate, a protein isolate, a soybean hull, a meal, a flour or an oil from the new soybean variety.

Advantageous Effects

*Aritaunkong*, which is a new soybean (*Glycine max*) variety according to an aspect of the present disclosure obtained by corssing IT109098 (a local collection, Naptegikong) as a mother plant with semi-wild K7-2 as a father plant, exhibits remarkably higher content of epicatechin, which is a functional ingredient of seed not rich in general soybean varieties, as 2 wt % or higher based on the total weight of an 80 wt % ethanol aqueous solution extract of the seed of the new soybean variety, than the mother plant IT109098, which has an epicatechin content of only 1 wt %, exhibits 2 times or higher antioxidant activity confirmed by DPPH radical-scavenging ability than the mother plant IT109098, and exhibits superior collagenase (matrix metalloproteinase-1, MMP-1) expression inhibition as compared to EGCG, which is known as an antiaging substance. Therefore, the new soybean variety according to an aspect of the present disclosure or a composition or functional health food containing an extract obtained from the new soybean variety exhibits superior antiaging or antioxidant effect, and epicatechin can be produced with high yield using the new soybean variety.

BRIEF DESCRIPTION OF DRAWINGS

FIG. 1 shows the genealogy of *Aritaunkong*, which is a new soybean (*Glycine max*) variety according to an aspect of the present disclosure.

BEST MODE

Figure 2:
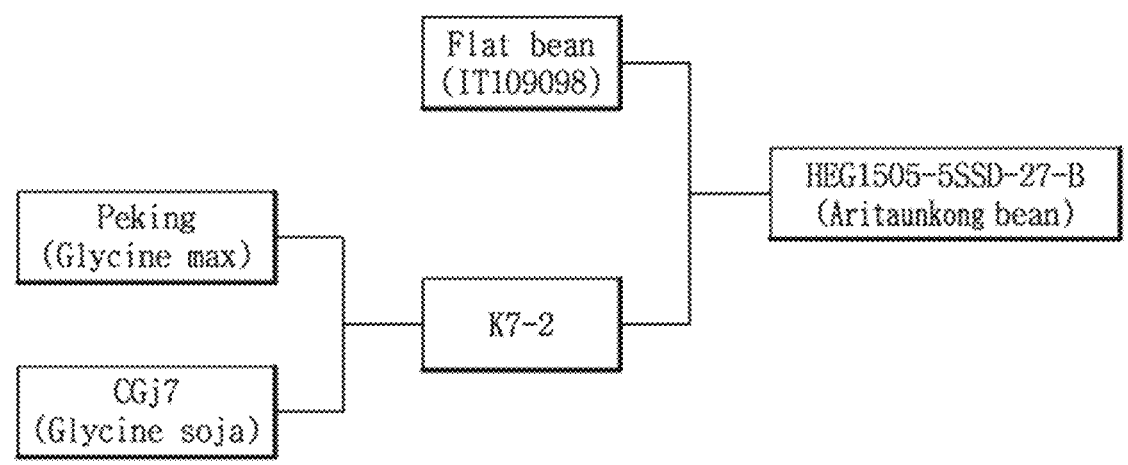
FIG. 2 shows the family tree of *Aritaunkong*, which is a new soybean (*Glycine max*) variety according to an aspect of the present disclosure.

Hereinafter, the present disclosure is described in detail.

In an aspect of the present disclosure, a "content" may be calculated based on an extract obtained by extracting a crushed seed, a plant or a part thereof at 20-30° C. for 12-36 hours using an 80 wt % ethanol aqueous solution. It is to be understood that the "content" described in the present disclosure is described as an example and may vary depending on the soil and weather conditions of cultivation, particular seeds, etc.

In an aspect of the present disclosure, the characteristics of a new soybean variety including seeds and the plant are assessed and tested according to "Guideline for characterization of crops for examination of new varieties—soybean (*Glycine max* (L) Merrill)(Korea Seed & Variety Service, Ministry of Agriculture, Food and Rural Affairs, http.//www.seed.go.kr)", which specifies the matters required for describing the characteristics of crop varieties according to the Guidance of Seed Management (Article 2, Table 1) pursuant to Article 30 of the Plant Variety Protection Act and Article 33 of the enforcement decree thereof and the methods for characterization necessary for cultivation examination set forth in Article 47 of the enforcement rules thereof, unless specified otherwise in the present disclosure. In addition, unless specified otherwise, it refers to the mean value of the quantitative character of the new soybean variety.

In an aspect of the present disclosure, "antioxidation" may include protection of the human body from oxidative stress or reactive oxygen species, specifically the protection of skin.

In an aspect, the present disclosure may provide a new soybean (*Glycine max*) variety obtained by corssing IT109098 (a local collection, Naptegikong) as a mother plant with semi-wild K7-2 as a father plant, wherein the new soybean variety may be a seed, a soybean plant or a part thereof. In addition, the present disclosure may provide a new soybean (*Glycine max*) variety obtained by corssing IT109098 as a mother plant with semi-wild K7-2 as a father plant, wherein the new soybean variety may be a new soybean variety having one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test.

Specifically, in an aspect, the present disclosure may provide a new soybean (*Glycine max*) variety obtained by corssing IT109098 as a mother plant with semi-wild K7-2 as a father plant. Specifically, the new soybean variety, specifically a seed thereof may contain epicatechin with a content of 2 wt % or more based on the total weight of an 80 wt % ethanol aqueous solution of the new soybean extract, specifically a seed thereof extract. More specifically, the new soybean variety may have an epicatechin content of 2 wt % or more, 2.1 wt % or more, 2.2 wt % or more, 2.3 wt % or more, 2.4 wt % or more, 2.5 wt % or more, 2.6 wt % or more, 2.7 wt % or more, 2.8 wt % or more, 2.9 wt % or more, 3 wt % or more, 3.1 wt % or more, 3.2 wt % or more, 3.3 wt % or more, 3.4 wt % or more, 3.5 wt % or more, 3.6 wt % or more, 3.7 wt % or more, 3.8 wt % or more, 3.9 wt % or more, 4 wt % or more, 4.1 wt % or more or 4.2 wt % or more based on the total weight of an 80 wt % ethanol aqueous solution extract of the new soybean variety. The new soybean variety may be one having a deposition number of KCTC14220BP, and a representative sample of the new soybean variety may have a deposition number of KCTC14220BP. Specifically, the seed of the new soybean variety may have a deposition number of KCTC14220BP, and a representative sample of the seed of the new soybean variety may have a deposition number of KCTC4220BP. In an example of the present disclosure, the epicatechin content of *Aritaunkong*, which is a soybean variety obtained by corssing IT109098 as a mother plant with semi-wild K7-2 as a father plant, was 4256.6 μg/g, which was remarkably higher than those of the mother plant IT109098 (1099.0 μg/g) or the father plant K7-2 (3425.7 μg/g). Therefore, it was confirmed that a composition or functional health food containing the new soybean variety according to an aspect of the present disclosure (e.g., soybean seed, soybean plant or pan thereof) or an extract thereof has superior antiaging or antioxidant effect, and epicatechin can be produced with high yield by using the new soybean variety (Test Example 3 and Table 7).

In addition, in an aspect of the present disclosure, the new soybean (*Glycine max*) variety may be one obtained by corssing IT109098 as a mother plant with semi-wild K7-2 as a father plant, and an extract of the new soybean variety, specifically an extract of the seed of the new soybean variety, may have $IC_{50}$ of 70 ppm or lower in antioxidant activity test through DPPH reduction. More specifically, an extract of the new soybean variety, specifically the seed of the new soybean variety, may have $IC_{50}$ of 70 ppm or lower, 69 ppm or lower, 68 ppm or lower, 67 ppm or lower, 66 ppm or lower, 65 ppm or lower, 64 ppm or lower, 63 ppm or lower, 62 ppm or lower, 61 ppm or lower, 60 ppm or lower, 59 ppm or lower, 58 ppm or lower, 57 ppm or lower, 56 ppm or lower, 55 ppm or lower, 54 ppm or lower, 53 ppm or lower, 52 ppm or lower, 51 ppm or lower, 50 ppm or lower, 49 ppm or lower, 48 ppm or lower, 47 ppm or lower, 46 ppm or lower, 45 ppm or lower, 44 ppm or lower, 43 ppm or lower, 42 ppm or lower, 41.8 ppm or lower, 41.6 ppm or lower or 41.4 ppm or lower in antioxidant activity test through DPPH reduction. The new soybean variety may have a deposition number of KCTC14220BP, and a representative sample of the new soybean variety may have a deposition number of KCTC14220BP. Specifically, the seed of the new soybean variety may have a deposition number of KCTC14220BP, a representative sample of the seed of the new soybean variety may have a deposition number of KCTC14220BP. In an example of the present disclosure, the DPPH radical-scavenging ability ($IC_{50}$) of *Aritaunkong*, which is a new soybean variety obtained by corssing IT109098 as a mother plant with semi-wild K7-2 as a father plant, was 41.4 ppm when tested in an antioxidant activity test through DPPH reduction, which was lower than those of the mother plant IT109098 (105.9 ppm) and the father plant K7-2 (73.4 ppm). The $IC_{50}$ of *Aritaunkong* was even lower than that of a positive control group (Trolox). Therefore, it was confirmed that a composition or functional health food containing the new soybean variety according to an aspect of the present disclosure (e.g., soybean seed, soybean plant or part thereof) or an extract thereof has superior antioxidant effect (Test Example 1 and Table 4).

In addition, in an aspect of the present disclosure, the new soybean (*Glycine max*) variety may be obtained by corssing IT109098 as a mother plant with semi-wild K7-2 as a father plant, and an extract of the new soybean variety, specifically an extract of the seed of the new soybean variety may exhibit collagenase expression inhibition of 60% or higher in collagenase expression inhibition test. More specifically, an extract of the new soybean variety, specifically the seed of the new soybean variety, may exhibit collagenase expression inhibition of 60% or higher, 60.5% or higher, 61% or higher, 61.5% or higher, 62% or higher, 62.5% or higher, 63% or higher, 63.5% or higher, 64% or higher, 64.5% or higher, 65% or higher, 65.5% or higher, 66% or higher, 66.5% or higher, 67% or higher, 67.5% or higher, 68% or higher, 68.5% or higher, 69% or higher or 69.5% or higher in collagenase expression inhibition test. The new soybean variety may have a deposition number of KCTC14220BP, and a representative sample of the new soybean variety may have a deposition number of KCTC14220BP. Specifically, the seed of the new soybean variety may have a deposition number of KCTC14220BP, and a representative sample of the seed of the new soybean variety may have a deposition number of KCTC14220BP. In an example of the present disclosure, the collagenase expression inhibition of *Aritaunkong*, which is a new soybean variety obtained by corssing IT109098 as a mother plant with semi-wild K7-2 as a father plant, evaluated by collagenase (MMP-1) expression inhibition test was 69.6%, which was higher than those of the mother plant IT109098 (50%) and the father plant K7-2 (26.1%). The collagenase expression inhibition by *Aritaunkong* was even higher than that of a positive control group (EGCG). Therefore, it was confirmed that a composition or functional health food containing the new soybean variety according to an aspect of the present disclosure (soybean seed, soybean plant or a part thereof) or an extract thereof has superior antiaging effect, e.g., skin antiaging effect (Test Example 2 and Table 5).

In an aspect of the present disclosure, the new soybean variety may have a deposition number of KCTC14220BP, and a representative sample of the new soybean variety may have a deposition number of KCTC14220BP.

In an aspect of the present disclosure, the new soybean variety may be a seed.

In an aspect of the present disclosure, the new soybean variety may be a soybean plant or a part thereof. Specifically, the soybean plant may be one obtained from the seed of the new soybean variety, more specifically one formed as the seed of the new soybean variety is germinated. In addition, a part of the soybean plant may be specifically pollen, root, seed coat, cell, leaf, stem, anther, ovule, bean sprout, pod or an extract thereof.

In an aspect of the present disclosure, the soybean plant may have the characteristics listed in Tables 1-3.

Specifically, the soybean plant may have the morphological characteristics of *Aritaunkong* listed in Table 1, more specifically one or more morphological characteristics of (1)-(11), further more specifically the morphological characteristics of (1)-(11):

(1) the hypocotyl is free from anthocyanin;
(2) the plant type is semi-horizontal;
(3) the trichome color of the main stem is brown;
(4) the stem length is 230-290 cm;
(5) the length/width ratio of the lateral leaflet is smaller as compared to IT109098;
(6) the lateral leaflet size is smaller as compared to IT109098;
(7) the flower is white;
(8) the pod color is dark brown as compared to IT109098;
(9) the seed size is smaller as compared to IT109098;
(10) the seed coat luster is weaker as compared to IT109098; and
(11) the color of the hypocotyl is green.

In an aspect of the present disclosure, the length/width ratio of the lateral leaflet, which is the morphological characteristic of (5), may be smaller, specifically as compared to IT109098.

In an aspect of the present disclosure, the lateral leaflet size, which is the morphological characteristic of (6), may be smaller, specifically as compared to IT109098.

In an aspect of the present disclosure, the pod color, which is the morphological characteristic of (8), may be dark brown, specifically as compared to IT109098.

In an aspect of the present disclosure, the seed size, which is the morphological characteristic of (9), may be smaller, specifically as compared to IT109098.

In an aspect of the present disclosure, the seed coat luster, which is the morphological characteristic of (10), may be weaker, specifically as compared to IT109098.

In addition, the soybean plant specifically may further have one or more morphological characteristics of (12)-(23), and more specifically may further have the morphological characteristics of (12)-(23):
(12) the growth habit is semi-indeterminate;
(13) the main stem has pubescence;
(14) the leaf surface is moderately protrusive;
(15) the lateral leaflet has a narrow leaflet (pointed oval shape);
(16) the greenness of the leaf is intermediate;
(17) the seed has a rectangular oval shape;
(18) the background color of the seed coat is medium brown;
(19) the seed coat has no bloom;
(20) the seed has yellow cotyledons;
(21) the seed has no net pattern;
(22) the seed has a dark brown hilum; and
(23) the raphe of the hilum of the seed and the seed coat has the same color.

In an aspect of the present disclosure, the soybean plant may have the crop characteristics of *Aritaunkong* listed in Tables 2 and 3, more specifically one or more crop characteristics of (1)-(4), further more specifically the crop characteristics of (1)-(4):
(1) the flower blooms later as compared to IT109098;
(2) the fruit ripens later as compared to IT109098;
(3) the number of pods is larger as compared to IT109098; and
(4) the recovery rate is higher as compared to IT109098.

In an aspect of the present disclosure, the soybean plant may have 29-35 pods.

Specifically, the soybean plant may have 29 or more, 30 or more, 31 or more, 32 or more, 33 or more, 34 or more or 35 or more pods, and 35 or less, 34 or less, 33 or less, 32 or less, 31 or less, 30 or less or 29 or less pods. In an example of the present disclosure, a plant obtained from the seed of *Aritaunkong*, which is a new soybean (*Glycine max*) variety obtained by corssing IT109098 as a mother plant with semi-wild K7-2 as a father plant, had more pods, 32 on average, than the mother plant IT109098 or the father plant K7-2 (Example 3 and Table 2).

In addition, in an aspect of the present disclosure, the soybean plant may have a recovery rate of 10% or higher. Specifically, the soybean plant may have a recovery rate of 10% or higher, 11% or higher, 12% or higher, 13% or higher, 14% or higher, 15% or higher, 16% or higher or 17% or higher. In an example of the present disclosure, the plant of *Aritaunkong*, which is a new soybean (*Glycine max*) variety obtained by corssing IT109098 as a mother plant with semi-wild K7-2 as a father plant, exhibited an average recovery rate (%) of 17%, which was higher than that of the mother plant IT109098 (0%)(Example 3 and Table 3).

In another aspect, the present disclosure may provide a method for producing a new soybean variety, which includes: corssing a soybean plant; and harvesting a soybean seed obtained from the corssing. The soybean plant may be a new soybean (*Glycine max*) variety obtained by corssing IT109098 as a mother plant with semi-wild K7-2 as a father plant. Specifically, it may be a soybean plant of the new soybean variety or a soybean plant obtained from the seed of the new soybean variety. More specifically, the soybean plant may be a soybean plant which is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test. More specifically, the soybean plant may have a deposition number of KCTC14220BP, or a representative sample of the new soybean variety may have a deposition number of KCTC14220BP. The same description about the soybean variety, seed, epicatechin, antioxidant activity, collagenase expression inhibition, soybean plant, a part thereof, etc. given above applies here.

In an aspect of the present disclosure, the method for producing the new soybean variety may further include: (a) producing a seed of a progeny plant of a subsequent generation by corssing a soybean plant that has grown from the soybean seed obtained from the selfing the soybean plant or crossing with another soybean plant; (b) producing a progeny plant of a further subsequent generation by growing the progeny plant of the subsequent generation from the seed of the progeny plant of the subsequent generation and selfing the progeny plant of the subsequent generation or crossing with a second plant; and (c) repeating the steps (a) and (b) by using the progeny plant of the further subsequent generation of the step (b) instead of the plant that has grown from the soybean seed obtained from the corssing in the step (a), wherein the steps (a) and (b) are repeated enough to produce an inbred plant from the high-yielding new soybean variety through inbreeding.

In an aspect of the present disclosure, the new soybean variety produced by the method for producing a new soybean variety may be an F1 soybean seed. That is to say, in another aspect, the present disclosure may provide an F1 seed produced by the method for producing a soybean seed.

In an aspect of the present disclosure, the new soybean variety produced by the method for producing the new soybean variety may be an F1 soybean plant produced by growing the F1 soybean seed or a part thereof. That is to say, in another aspect, the present disclosure may provide an F1 soybean plant produced by growing the F1 seed or a part thereof.

In an aspect of the present disclosure, the method for producing the new soybean variety may further include applying plant breeding to the soybean plant or a part thereof and may be developing a second soybean plant through the plant breeding. That is to say, in another aspect, the present disclosure may provide a method for developing a second soybean plant through plant breeding, which includes applying plant breeding to the F1 soybean plant or a part thereof.

In an aspect of the present disclosure, the method for producing the new soybean variety may include: (a) artificially corssing IT109098 as a mother plant with semi-wild K7-2 as a father plant during a flowering season; (b) harvesting an F6 generation seed by advancing F1-F5 generations of the crossbred plant by a single seed descent (SSD) method; and (c) selecting one final pedigree by seeding the harvested F6 generation seed by a pedigree breeding method and conducting productivity and characteristics testing, wherein the one final pedigree has one or more of the following characteristics: (1) the epicatechin content of the seed is 2 wt % or higher based on the total weight of an 80 wt % ethanol aqueous solution extract of the seed; (2) the extract of the seed exhibits $IC_{50}$ of 70 ppm or lower in antioxidant activity test through DPPH reduction; and (3) the extract of the seed exhibits collagenase expression inhibition of 60% or higher in collagenase expression inhibition test. That is to say, in another aspect, the present disclosure may provide a method for breeding a soybean variety, which includes: (a) artificially corssing IT109098 as a mother plant with semi-wild K7-2 as a father plant during a flowering season; (b) harvesting an F6 generation seed by advancing F1-F5 generations of the crossbred plant by a single seed descent (SSD) method; and (c) selecting one final pedigree by seeding the harvested F6 generation seed by a pedigree breeding method and conducting productivity and characteristics testing, wherein the one final pedigree has one or more of the following characteristics: (1) the epicatechin content of the seed is 2 wt % or higher based on the total weight of an 80 wt % ethanol aqueous solution extract of the seed; (2) the extract of the seed exhibits $IC_{50}$ of 70 ppm or lower in antioxidant activity test through DPPH reduction; and (3) the extract of the seed exhibits collagenase expression inhibition of 60% or higher in collagenase expression inhibition test.

In another aspect, the present disclosure may provide an antiaging composition containing an extract of the new soybean variety as an active ingredient. In addition, the present disclosure may provide an antioxidant composition containing an extract of the new soybean variety as an active ingredient. The new soybean variety may be anew soybean (*Glycine max*) variety obtained by corssing IT109098 as a mother plant with semi-wild K7-2 as a father plant, specifically a seed, a soybean plant or a part thereof of the new soybean variety. More specifically, the new soybean variety may be a new soybean variety which is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits ICs of 70 ppm or lower in antioxidant activity test through DPPH reduction; and (3) the extract of the new soybean variety exhibits collagenase expression inhibition of 60% or higher in collagenase expression inhibition test. More specifically, it may be a new soybean variety having a deposition number of KCTC14220BP or a representative sample of the new soybean variety having a deposition number of KCTC4220BP. The new soybean variety may be a seed. Alternatively, the new soybean variety may be a soybean plant or a part thereof. Specifically, the soybean plant may be a plant having one or more morphological characteristics of (1)-(23), one or more crop characteristics of (1)-(4) or the characteristics listed in Tables 1-3. The same description about the new soybean variety, seed, soybean plant, part thereof, epicatechin, antioxidant activity, collagenase expression inhibition, etc. given above applies here.

In an aspect of the present disclosure, the extract of the new soybean variety may include a crude extract or a fraction obtained by further fractionating the extract. Specifically, the extract of the new soybean variety may be a crude extract of the new soybean variety, a fraction thereof or a combination thereof. The crude extract refers to one that is obtained by contacting the new soybean variety with an extraction solvent. The fraction refers to one that has been separates from the crude extract and contains specific ingredients. The extract or a fraction thereof may contain an extract of the new soybean variety, a fraction thereof, a subfraction thereof or a mixture thereof. The subfraction may be one obtained by passing through an ultrafiltration membrane having a cut-off value, or may be one obtained by column chromatography or solvent fractionation.

In an aspect of the present disclosure, the separation may be achieved by filtration, submersion, centrifugation, solvent fractionation, chromatography or a combination thereof. The chromatography may be one designed for separation under various conditions, i.e., size, charge hydrophobicity or affinity, and may be ion exchange chromatography, affinity chromatography, size-exclusion chromatography, high-performance liquid chromatography (HPLC), high-speed liquid chromatography, column chromatography, reversed-phase column chromatography or a combination thereof.

In an aspect of the present disclosure, the extraction may include incubation of the new soybean variety, specifically a seed, a soybean plant or a part thereof, for a predetermined time in a solvent. The extraction may be performed with or without stirring, or may include heating. The incubation may be performed with or without stirring at room temperature to reflux temperature. The incubation temperature may be selected adequately depending on the selected solvent. For example, the incubation may be performed at room temperature to reflux temperature, at 30° C. to reflux temperature, or at 40° C. to reflux temperature. The heating may be performed to 50° C., 60° C., 70° C., 80° C. or reflux temperature. The heating may be performed at 50° C. to reflux temperature, 60° C. to reflux temperature, 70° C. to reflux temperature, 80° C. to reflux temperature, or reflux temperature. The extraction time may vary depending on the selected temperature. The extraction time may be from 1 hour to 2 months, e.g., from 1 hour to 1 month, from 1 hour to 15 days, from 1 hour to 10 days, from 1 hour to 5 days, from 1 hour to 3 days, from 1 hour to 2 days, from 1 hour to 1 day, from 5 hours to 1 month, from 5 hours to 15 days, from 5 hours to 10 days, from 5 hours to 5 days, from 5 hours to 3 days, from 5 hours to 2 days, from 5 hours to 1 day, from 10 hours to 1 month, from 10 hours to 15 days, from 10 hours to 10 days, from 10 hours to 5 days, from 10 hours to 3 days, or from 10 hours to 2 days. The extraction may be performed by reflux extraction of the seed, soybean plant or apart thereof in a solvent. The volume of the solvent may be 1 time, 2 times, 5 times, 10 times or 15 times or more based on the weight of the seed, soybean plant or a part thereof. The volume of the solvent may be 1-15 times, 2-15 times, 5-15 times, 10-15 times or about 15 times based on the weight of the soybean plant. The seed, soybean plant or a part thereof may be one dried in the shade, using a light-shielding device, with hot air or using a dryer.

In an aspect of the present disclosure, the extraction may be performed by a common method in the art such as filtration, hot water extraction, submersion extraction, cold extraction, microwave extraction, reflux condensation extraction, autoclave extraction, subcritical extraction, supercritical extraction, ultrasonic extraction, etc. For example, submersion extraction may be used. The submersion extraction may be performed at elevated temperature or room temperature, and may be carried out 1-5 times. The new soybean variety may be contacted with 0.1-10 times or 1-6 times of an extraction solvent. The cold extraction temperature may be 20-40° C. The warm or hot extraction temperature may be 40-100° C. The cold extraction may be performed for 24-120 hours, and the warm or hot extraction may be performed for 0.5-48 hours.

In an aspect of the present disclosure, the extraction may include removal of the solvent from the obtained extract by a well-known method such as evaporation or concentration under reduced pressure. The extraction may also include preparation of a dried extract by drying the obtained extract such as freeze-drying. The concentration under reduced pressure may be performed using a vacuum concentrator or a vacuum rotatory evaporator. And, the drying may be performed by decompression drying, vacuum drying, boiling drying, spray drying or freeze-drying.

In an aspect of the present disclosure, the extract may be obtained by extracting the new soybean variety with a solvent selected from a group consisting of water, a $C_1$-$C_6$ alcohol and a mixture thereof. The alcohol may be a $C_1$-$C_3$, $C_1$-$C_4$, $C_1$-$C_5$ or $C_1$-$C_6$ alcohol. The alcohol may be a primary alcohol. The Ci-C alcohol may be methanol, ethanol, propanol, isopropanol, butanol or a mixture thereof.

In an aspect of the present disclosure, the content of the extract may be 0.001-99.9 wt %, specifically 0.001 wt % or more, 0.01 wt % or more, 0.1 wt % or more, 1 wt % or more, 10 wt % or more, 20 wt % or more, 40 wt % or more, 60 wt % or more or 80 wt % or more and 99.9 wt % or less, 90 wt % or less, 80 wt % or less, 60 wt % or less, 40 wt % or less, 20 wt % or less, 10 wt % or less, 1 wt % or less, 0.1 wt % or less or 0.01 wt % or less, based on the total weight of the composition.

In an example of the present disclosure, *Aritaunkong*, which is a new soybean (*Glycine max*) variety according to an aspect of the present disclosure obtained by corssing IT109098 as a mother plant with semi-wild K7-2 as a father plant, had a remarkably higher epicatechin content of 2 wt % or more based on the total weight of an 80 wt % ethanol aqueous solution of seed extract than the mother plant IT109098 (1 wt %), exhibited 2 times or higher DPPH radical-scavenging ability than the mother plant IT109098, and exhibited higher collagenase expression inhibition than EGCG known as an antiaging substance. Therefore, it was confirmed that a composition containing the new soybean variety according to an aspect of the present disclosure or an extract thereof has superior antiaging or antioxidant effect (Test Examples 1-3).

In an aspect of the present disclosure, the composition may be a food composition, a cosmetic composition or a pharmaceutical composition.

In an exemplary embodiment, the food composition includes a functional health food composition, and the functional health food composition may be for improving, alleviating or preventing a disease caused by oxidative stress or reactive oxygen species. Specifically, the disease caused by oxidative stress or reactive oxygen species may be one or more selected from a group consisting of cancer, arteriosclerosis, diabetes, stroke, myocardial infarction, hepatitis, nephritis, atopy, degenerative dementia, inflammatory disease, sepsis, aging, skin aging, muscle atrophy, autoimmune disease, asthma, chronic bronchitis, lung disease, chronic heart failure, kidney disease, rheumatism, arthritis, joint disease, Alzheimer's disease, Parkinson's disease, memory decline, depression, brain disease, cataract, retinal disease, eye disease, hypertension, ischemia, cardiomyopathy, cardiac arrest, cardiovascular disease, toxemia of pregnancy, intrauterine growth restriction, fetal abnormality and neurodegenerative disease.

In an exemplary embodiment, the food composition may include a functional health food composition, and the functional health food composition may be for improving, alleviating or preventing aging-related diseases, specifically skin aging-related diseases. More specifically, the aging-related disease may be one or more selected from a group consisting of skin wrinkles, photoaging, melanosis, skin pigmentation, skin burn, skin inflammation and skin cancer.

The functional health food composition includes food additives or functional foods of various types. The composition may be processed into leached tea, liquid tea, beverages, fermented milk, cheese, yogurt, juice, probiotics, health supplements, etc. and may be used in the form of various food additives.

In an exemplary embodiment, the cosmetic composition may be provided as any formulation suitable for topical application. For example, it may be formulated as a solution, an oil-in-water emulsion, a water-in-oil emulsion, a suspension, a solid, a gel, a powder, a paste, a foam or an aerosol composition. These formulations may be prepared according to common methods in the art.

In an exemplary embodiment, the cosmetic composition may specifically contain, in addition to the above-described substance, other ingredients that may provide a synergistic effect to the main effect within a range not negatively affecting the main effect. The cosmetic composition according to the present disclosure may contain a substance selected from a group consisting of a vitamin, a polypeptide, a polysaccharide and a sphingolipid. In addition, the cosmetic composition may further contain a humectant, an emollient, a surfactant, a UV absorbent, an antiseptic, a sterilizer, an antioxidant, a pH control agent, an organic or inorganic pigment, a flavorant, a cooling agent or an antiperspirant. The content of these ingredients may be determined adequately by those skilled in the art within a range not negatively affecting the purpose and effect of the present disclosure. The content may be 0.01-5 wt %, specifically 0.01-3 wt %, based on the total weight of the composition.

In an exemplary embodiment, the pharmaceutical composition may be for preventing or treating a disease caused by oxidative stress or reactive oxygen species. Specifically, the disease caused by oxidative stress or reactive oxygen species may be one or more selected from a group consisting of cancer, arteriosclerosis, diabetes, stroke, myocardial infarction, hepatitis, nephritis, atopy, degenerative dementia, inflammatory disease, sepsis, aging, skin aging, muscle atrophy, autoimmune disease, asthma, chronic bronchitis, lung disease, chronic heart failure, kidney disease, rheumatism, arthritis, joint disease, Alzheimer's disease, Parkinson's disease, memory decline, depression, brain disease, cataract, retinal disease, eye disease, hypertension, ischemia, cardiomyopathy, cardiac arrest, cardiovascular disease, toxemia of pregnancy, intrauterine growth restriction, fetal abnormality and neurodegenerative disease.

In an exemplary embodiment, the pharmaceutical composition may be for preventing or treating an aging-related disease, specifically a skin aging-related disease. More specifically, the aging-related disease may be one or more selected from a group consisting of skin wrinkles, photoaging, melanosis, skin pigmentation, skin burn, skin inflammation and skin cancer.

Also, in an exemplary embodiment, the pharmaceutical composition may be provided in the form of any formulation suitable for application. For example, it may be administered orally, transdermally, intravenously, intramuscularly or subcutaneously. In an exemplary embodiment, the pharmaceutical composition may be an injection, a solution for external application to skin, a suspension, an emulsion, a gel, a patch or a spray, although not being limited thereto. These formulations may be prepared easily according to common methods in the art, and a surfactant, an excipient, a wetting agent, an emulsification accelerator, a suspending agent, a salt or buffer for control of osmotic pressure, a colorant, a flavor, a stabilizer, antiseptic, a preservative or other commonly used adjuvants may be used adequately.

An effective amount of the pharmaceutical composition according to the present disclosure will vary depending on the age, sex and body weight of a subject, pathological condition and severity thereof, administration route or the discretion of a prescriber. Determination of dosage based on these factors is within the level of those skilled in the art. A daily dosage may be, for example, 0.1-5000 mg/kg/day, more specifically 50-500 mg/kg/day, although not being limited thereto.

In another aspect, the present disclosure may provide a functional health food containing the new soybean variety. The new soybean variety may be a new soybean (*Glycine max*) variety obtained by corssing IT109098 as a mother plant with semi-wild K7-2 as a father plant. Specifically, it may be a seed of the new soybean variety, a soybean plant or a part thereof. More specifically, the new soybean variety may be a new soybean variety which is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test. More specifically, the new soybean variety may have a deposition number of KCTC14220BP, or a representative sample of the new soybean variety may have a deposition number of KCTC14220BP. The new soybean variety may be a seed. Alternatively, the new soybean variety may be a soybean plant or a part thereof. Specifically, the soybean plant may be a plant having one or more morphological characteristics of (1)-(23), one or more crop characteristics of (1)-(4) or the characteristics listed in the characteristics listed in Tables 1-3. The description about the new soybean variety, seed, soybean plant, part thereof, epicatechin, antioxidant activity, collagenase expression inhibition, etc. given above applies here.

In another aspect, the present disclosure may provide a method for producing epicatechin, which includes extracting epicatechin from the new soybean variety. The new soybean variety may be a new soybean (*Glycine max*) variety obtained by corssing IT109098 as a mother plant with semi-wild K7-2 as a father plant. Specifically, it may be a seed of the new soybean variety, a soybean plant or a part thereof. More specifically, the new soybean variety may be anew soybean variety which is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test. More specifically, it may be a new soybean variety having a deposition number of KCTC14220BP, or a representative sample of the new soybean variety having a deposition number of KCTC14220BP. The new soybean variety may be a seed. Alternatively, the new soybean variety may be a soybean plant or a part thereof. Specifically, the soybean plant may be a plant having one or more morphological characteristics of (1)(23), one or more crop characteristics of (1)-(4) or the characteristics listed in the characteristics listed in Tables 1-3. The description about the new soybean variety, seed, soybean plant, part thereof, epicatechin, antioxidant activity, collagenase expression inhibition, etc. given above applies here.

In an example of the present disclosure, *Aritaunkong*, which is a new soybean (*Glycine max*) variety according to an aspect of the present disclosure obtained by corssing IT109098 as a mother plant with semi-wild K7-2 as a father plant, had a remarkably higher epicatechin content of 2 wt % or more based on the total weight of an 80 wt % ethanol aqueous solution of seed extract, as compared to that of the mother plant IT109098 (1 wt %). Therefore, epicatechin can be produced with very high yield by using the new soybean variety according to an aspect of the present disclosure (Test Example 3 and Table 7).

In another aspect, the present disclosure may provide a method for producing a commodity plant product, which includes obtaining the new soybean variety; and producing commodity plant product including a protein concentrate, a protein isolate, a soybean hull, a meal, a flour or an oil from the new soybean variety. The new soybean variety may be a new soybean (*Glycine max*) variety obtained by corssing IT109098 as a mother plant with semi-wild K7-2 as a father plant. Specifically, it may be a seed of the new soybean variety, a soybean plant or apart thereof. More specifically, the new soybean variety may be a new soybean variety which is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test. More specifically, it may be a new soybean variety having a deposition number of KCTC14220BP, or a representative sample of the new soybean variety having a deposition number of KCTC14220BP. The new soybean variety may be a seed. Alternatively, the new soybean variety may be a soybean plant or a part thereof. Specifically, the soybean plant may be a plant having one or more morphological characteristics of (1)-(23), one or more crop characteristics of (1)-(4) or the characteristics listed in the characteristics listed in Tables 1-3. The description about the new soybean variety, seed, soybean plant, part thereof, epicatechin, antioxidant activity, collagenase expression inhibition, etc. given above applies here.

In an aspect of the present disclosure, the step of obtaining the new soybean variety may include producing the seed of new soybean variety according to an aspect of the present disclosure or obtaining a soybean plant or a part thereof by germinating or growing the seed of the new soybean variety. The growth may include not only soil cultivation but also hydroponic cultivation. The step may also include cutting or pulverizing the soybean plant or a part thereof. When the part is a seed, it may include pulverizing or hulling the seed.

In an aspect of the present disclosure, the step of producing the product from the new soybean variety may vary depending on the selected product. When the product is an extract, it may include an extraction process. When the product is an oil, it may include a process of extracting oil by press. The product may include a protein concentrate, a protein isolate, a soybean hull, a meal, a flour, an oil, an extract or a bean sprout.

In an example of the present disclosure, Aritaunkong, which is a new soybean (Glycine max) variety according to an aspect of the present disclosure obtained by corssing IT109098 as a mother plant with semi-wild K7-2 as a father plant, had a remarkably higher epicatechin content of 2 wt % or more based on the total weight of an 80 wt % ethanol aqueous solution extract of the new soybean variety, as compared to mother plant IT109098 (1 wt %), exhibited 2 times or higher DPPH radical-scavenging ability than the mother plant IT109098, and exhibited higher collagenase expression inhibition than EGCG known as an antiaging substance. Therefore, it was confirmed that a commodity plant product produced using a seed of the new soybean variety according to an aspect of the present disclosure, a soybean plant or a part thereof has superior antiaging or antioxidant effect (Test Example 1-3).

In another aspect, the present disclosure may provide a use of a new soybean (Glycine max) variety or an extract thereof for preparation of a food composition for antioxidation, wherein the new soybean variety is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test. The food composition for antioxidation may be for improving, alleviating or preventing a disease caused by oxidative stress or reactive oxygen species.

Specifically, the disease caused by oxidative stress or reactive oxygen species may be one or more selected from a group consisting of cancer, arteriosclerosis, diabetes, stroke, myocardial infarction, hepatitis, nephritis, atopy, degenerative dementia, inflammatory disease, sepsis, aging, skin aging, muscle atrophy, autoimmune disease, asthma, chronic bronchitis, lung disease, chronic heart failure, kidney disease, rheumatism, arthritis, joint disease, Alzheimer's disease, Parkinson's disease, memory decline, depression, brain disease, cataract, retinal disease, eye disease, hypertension, ischemia, cardiomyopathy, cardiac arrest, cardiovascular disease, toxemia of pregnancy, intrauterine growth restriction, fetal abnormality and neurodegenerative disease. The description about the seed of the soybean variety, soybean plant, a part thereof, extract, etc. given above also applies here.

In another aspect, the present disclosure may provide a use of a new soybean (Glycine max) variety or an extract thereof for preparation of a cosmetic composition for antioxidation, wherein the new soybean variety is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test. The description about the new soybean variety, extract, etc. given above also applies here.

In another aspect, the present disclosure may provide a use of a new soybean (Glycine max) variety or an extract thereof for preparation of a pharmaceutical composition for antioxidation, wherein the new soybean variety is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test. The pharmaceutical composition for antioxidation may be for preventing or treating a disease caused by oxidative stress or reactive oxygen species. Specifically, the disease caused by oxidative stress or reactive oxygen species may be one or more selected from a group consisting of cancer, arteriosclerosis, diabetes, stroke, myocardial infarction, hepatitis, nephritis, atopy, degenerative dementia, inflammatory disease, sepsis, aging, skin aging, muscle atrophy, autoimmune disease, asthma, chronic bronchitis, lung disease, chronic heart failure, kidney disease, rheumatism, arthritis, joint disease, Alzheimer's disease, Parkinson's disease, memory decline, depression, brain disease, cataract, retinal disease, eye disease, hypertension, ischemia, cardiomyopathy, cardiac arrest, cardiovascular disease, toxemia of pregnancy, intrauterine growth restriction, fetal abnormality and neurodegenerative disease. The description about the new soybean variety, extract, etc. given above also applies here.

In another aspect, the present disclosure may provide a use of a new soybean (Glycine max) variety or an extract thereof for preparation of a food composition for antiaging, wherein the new soybean variety is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test. The food composition for antiaging may be for improving, alleviating or preventing an aging-related disease, specifically a skin aging-related disease. More specifically, the aging-related disease may be one or more selected from a group consisting of skin wrinkles, photoaging, melanosis, skin pigmentation, skin burn, skin inflammation and skin cancer.

In another aspect, the present disclosure may provide a use of a new soybean (*Glycine max*) variety or an extract thereof for preparation of a cosmetic composition for antiaging, wherein the new soybean variety is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test. The description about the new soybean variety, extract, etc. given above also applies here.

In another aspect, the present disclosure may provide a use of a new soybean (*Glycine max*) variety or an extract thereof for preparation of a pharmaceutical composition for antiaging, wherein the new soybean variety is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test. The pharmaceutical composition for antiaging may be for preventing or treating an aging-related disease, specifically a skin aging-related disease. More specifically, the aging-related disease may be one or more selected from a group consisting of skin wrinkles, photoaging, melanosis, skin pigmentation, skin burn, skin inflammation and skin cancer.

In another aspect, the present disclosure may provide a method for antioxidation, a method for alleviating, improving or preventing a disease caused by oxidative stress or reactive oxygen species, or a method for preventing or treating a disease caused by oxidative stress or reactive oxygen species, which includes administering a new soybean (*Glycine max*) variety or an extract thereof, wherein the new soybean variety is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test, to a subject in need of alleviation, improvement, prevention or treatment of a disease caused by oxidative stress or reactive oxygen species. The description about the new soybean variety, extract, antioxidation, administration type, administration dosage, administration method, etc. given above also applies here.

In another aspect, the present disclosure may provide a method for antiaging, a method for alleviating, improving or preventing an aging-related disease, or a method for preventing or treating an aging-related disease, which includes administering a new soybean (*Glycine max*) variety or an extract thereof, wherein the new soybean variety is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test, to a subject in need of alleviation, improvement, prevention or treatment of an aging-related disease, specifically a skin aging-related disease. The description about the new soybean variety, extract, antiaging, administration type, administration dosage, administration method, etc. given above also applies here.

In another aspect, the present disclosure may relate to a use of a new soybean (*Glycine max*) variety or an extract thereof for antioxidation, wherein the new soybean variety is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test.

In another aspect, the present disclosure may relate to a use of a new soybean (*Glycine max*) variety or an extract thereof for antiaging, wherein the new soybean variety is obtained by corssing IT109098 as a mother plant with semi-wild K7-2 as a father plant and has one or more of the following characteristics: (1) the epicatechin content of the new soybean variety is 2 wt % or higher based on the total weight of an 80 wt % ethanol aqueous solution extract of the new soybean variety; (2) the extract of the new soybean variety exhibits $IC_{50}$ of 70 ppm or lower in antioxidant activity test through DPPH reduction; and (3) the extract of the new soybean variety exhibits collagenase expression inhibition of 60% or higher in collagenase expression inhibition test.

Hereinafter, the present disclosure will be described more specifically through examples, preparation examples and test examples. However, the following examples, preparation examples and test examples are provided only to help the understanding of the present disclosure, and the scope of the present disclosure is not limited by them.

[Example 1] Breeding of New Soybean Variety

For development of a new soybean variety having increased epicatechin content and enhanced antiaging and antioxidant activity according to an aspect of the present disclosure, a new soybean variety was bred as follows.

First, in order to introduce genes expressing epicatechin and antioxidant activity into the native soybean (*Glycine max*) species, the Korean native species IT109098 (Korea National Institute of Agricultural Sciences, National Agrobiodiversity Center) as a mother plant was artificially crossbred in 2015 with semi-wild K7-2 with high epicatechin and antioxidant activity (Seoul National University Crop Genomics Lab, Professor Suk-la Lee) as a father plant. F1 seeds (crossbred HEG1505) were obtained and seven F1 plants were grown in the winter of 2015. In the summer of 2016, 250 F2 plants were advanced by the single seed descent method and 178 F3 plants were generation-accelerated in a temperature-controlled greenhouse in the winter. In 2017, 177 F4 plants were generation-accelerated in the summer and 117 F5 plants were generation-accelerated in the winter. In the summer of 2018, 117 F6 plants were advanced by the pedigree breeding method. In 2019, 10 pedigrees were selected in consideration of functionalities, agricultural characteristics, etc. and productivity and characteristics were tested. Finally, HEG1505-5SSD-27 was identified as the most superior pedigree in terms of agricultural characteristics, epicatechin content, DPPH radical-scavenging ability ($IC_{50}$) and collagenase (MMP-1) expression inhibition (%), and was named "Aritaunkong". The Aritaunkong was deposited in the Korea Research Institute of Bioscience and Biotechnology as KCTC14220BP.

Figure 1:
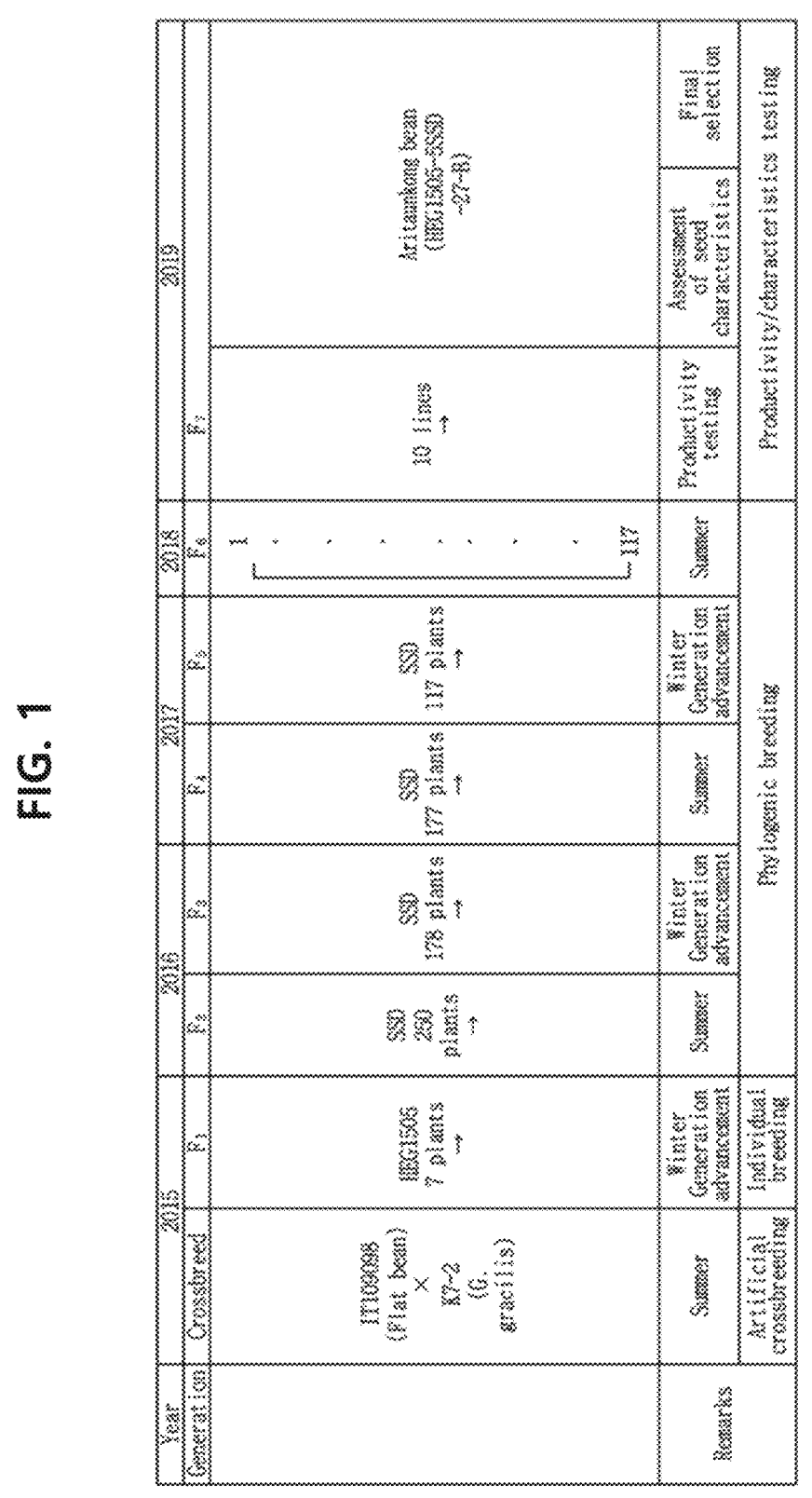
Figure 3A:
FIG. 3A shows the photograph of the seeds of IT109098, which is a mother plant of *Aritaunkong*, a new soybean (*Glycine max*) variety according to an aspect of the present disclosure.
Figure 3B:
FIG. 3B shows the photograph of the seeds of K7-2, which is a father plant of *Aritaunkong*, a new soybean (*Glycine max*) variety according to an aspect of the present disclosure.
Figure 3C:
FIG. 3C shows the photograph of the seeds of *Aritaunkong*, a new soybean (*Glycine max*) variety according to an aspect of the present disclosure.

FIG. 1 shows the genealogy of Aritaunkong, and FIG. 2 shows the family tree of Aritaunkong. FIG. 3A shows the photograph of the seeds of IT109098, FIG. 3B shows the photograph of the seeds of K7-2, and FIG. 3C shows the photograph of the seeds of the finally selected Aritaunkong.

[Example 2] Morphological Characteristics of Bred Pedigree

The morphological characteristics of the Aritaunkong bred in Example 1 were measured as follows.

Specifically, the Aritaunkong and IT109098 as a control soybean pedigree were seeded on Jun. 5, 2019 in the coarse loamy soil of Suwon (Scodun-dong, Gwonseon-gu, Suwon-si). The morphological characteristics of each plant were measured during the maturing period. Seeds were harvested on October 16 and their characteristics were measured. The result is shown in Table 1. The cultivation was performed on bare ground with intervals of 80×20 cm.

TABLE 1

Comparison of morphological characteristics of Ahrittaun bean and IT109098

| No. | Characteristics | Phenotype | Class | Ahrittaun bean Class mark | Measurement | IT09098 Class mark | Measurement |
|---|---|---|---|---|---|---|---|
| 1 | Hypocotyl: presence of anthocyanin | No | 1 | 1 | | 9 | |
| | | Yes | 9 | | | | |
| 2 | Hypocotyl: intensity of anthocyanin | Very weak | 1 | 1 | | 5 | |
| | | Weak | 3 | | | | |
| | | Moderate | 5 | | | | |
| | | Strong | 7 | | | | |
| | | Very strong | 9 | | | | |
| 3 | Plant: growth habit | Determinate | 1 | 3 | | 3 | |
| | | Quasi-determinate | 2 | | | | |
| | | Quasi-indeterminate | 3 | | | | |
| | | Indeterminate | 4 | | | | |
| 4 | Plant: type | Upright | 1 | 4 | | 3 | |
| | | Semi-upright | 2 | | | | |
| | | Intermediate | 3 | | | | |
| | | Semi-horizontal | 4 | | | | |
| | | Horizontal | 5 | | | | |
| 5 | Plant: trichome color of main stem | Gray | 1 | 2 | | 1 | |
| | | Yellowish brown | 2 | | | | |
| 5.1 | Plant: presence of fluffs in main stem | No | 1 | 9 | | 9 | |
| | | Yes | 9 | | | | |
| 6 | Plant: stem length (maturing period) | Very short | 1 | 9 | 261 cm | 9 | 214 cm |
| | | Short | 3 | | | | |
| | | Intermediate | 5 | | | | |
| | | Long | 7 | | | | |
| | | Very long | 9 | | | | |
| 7 | Leaf: protrusion of surface (blistering) | None or very weak | 1 | 5 | | 5 | |
| | | Weak | 3 | | | | |
| | | Intermediate | 5 | | | | |
| | | Strong | 7 | | | | |
| | | Very strong | 9 | | | | |
| 8 | Leaf: shape of lateral leaflet | Lanceolate | 1 | 3 | | 3 | |
| | | Deltoid | 2 | | | | |
| | | Round ovate | 3 | | | | |
| | | Pointed ovate | 4 | | | | |
| | | Rhomboid | 5 | | | | |
| 8.1 | Leaf: length/width ratio of lateral leaflet | Small | 3 | 3 | | 5 | |
| | | Intermediate | 5 | | | | |
| | | Large | 7 | | | | |
| 9 | Leaf: size of lateral leaflet | Small | 3 | 3 | | 5 | |
| | | Intermediate | 5 | | | | |
| | | Large | 7 | | | | |
| 10 | Leaf: degree of greenness | Weak | 3 | 5 | | 5 | |
| | | Intermediate | 5 | | | | |
| | | Strong | 7 | | | | |

TABLE 1-continued

Comparison of morphological characteristics of Ahrittaun bean and IT109098

| No. | Characteristics | Phenotype | Class | Ahrittaun bean Class mark | Ahrittaun bean Measurement | IT09098 Class mark | IT09098 Measurement |
|---|---|---|---|---|---|---|---|
| 11 | Flower: color | White | 1 | 1 | | 2 | |
| | | Violet | 2 | | | | |
| 12 | Seed: degree of brownness | Gray | 1 | 7 | | 5 | |
| | | Light brown | 3 | | | | |
| | | Brown | 5 | | | | |
| | | Dark brown | 7 | | | | |
| | | Black | 9 | | | | |
| 13 | Seed: size | Small | 3 | 3 | 8.8 g/100 seeds | 3 | 11.1 g/100 seeds |
| | | Intermediate | 5 | | | | |
| | | Large | 7 | | | | |
| 14 | Seed: shape | Spherical | 1 | 4 | | 4 | |
| | | Oblate | 2 | | | | |
| | | Oblong | 3 | | | | |
| | | Prolate oblong | 4 | | | | |
| 15 | Seed: background color of seed coat (excluding hilum) | Yellow | 1 | 5 | | 5 | |
| | | Greenish yellow | 2 | | | | |
| | | Green | 3 | | | | |
| | | Light brown | 4 | | | | |
| | | Medium brown | 5 | | | | |
| | | Dark brown | 6 | | | | |
| | | Black | 7 | | | | |
| | | Yellowish white | 8 | | | | |
| 15.1 | Seed: secondary color/shape of seed coat | Striped/spotted | 1 | — | | — | |
| | | | 2 | | | | |
| 15.2 | Seed: luster of seed coat | Weak | 3 | 3 | | 5 | |
| | | Intermediate | 5 | | | | |
| | | Strong | 7 | | | | |
| 15.3 | Seed: presence of bloom (white powder) in seed coat | No | 1 | 1 | | 1 | |
| | | Yes | 9 | | | | |
| 15.3 | Seed: color of cotyledon | Yellow | 1 | 1 | | 1 | |
| | | Green | 2 | | | | |
| 15.4 | Seed: presence of net pattern | No | 1 | 1 | | 1 | |
| | | Yes | 9 | | | | |
| 16 | Seed: discoloration of seed coat by peroxidase | No | 1 | — | | — | |
| | | Yes | 9 | | | | |
| 17 | Seed: color of hilum | Gray | 1 | 4 | | 4 | |
| | | Yellow | 2 | | | | |
| | | Light brown | 3 | | | | |
| | | Dark brown | 4 | | | | |
| | | Incompletely black | 5 | | | | |
| | | Black | 6 | | | | |
| 18 | Seed: funiculus color of hilum | Same color as seed coat | 1 | 1 | | 1 | |
| | | Different color from seed coat | 2 | | | | |

As shown in Table 1, the *Aritaunkong* of Example 1 has the following morphological characteristics, and some of the following characteristics are distinguished from those of IT109098:

(1) the hypocotyl is free from anthocyanin.
(2) the growth habit is semi-indeterminate.
(3) the plant type is semi-horizontal.
(4) the trichome color of the main stem is brown.
(5) the main stem has pubescence.
(6) the stem length is very long.
(7) the leaf surface is moderately protrusive.
(8) the lateral leaflet has a narrow leaflet.
(9) the length/width ratio of lateral leaflet is small.
(10) the lateral leaflet has a small size.
(11) the color of the hypocotyl is green
(12) the greenness of the leaf is intermediate.
(13) the flower is white.
(14) the pod is dark brown.
(15) the seed has a small size.
(16) the seed has a rectangular oval shape.
(17) the background color of the seed coat is medium brown.
(18) the seed coat has weak luster.
(19) the seed coat has no bloom.
(20) the seed has yellow cotyledons.
(21) the seed has no net pattern.
(22) the seed has a dark brown hilum.
(23) the raphe of the hilum of the seed and the seed coat has the same color.

[Example 3] Crop Characteristics of Bred Pedigree

The crop characteristics of the *Aritaunkong* bred in Example 1 are shown in Tables 2 and 3.

TABLE 2

Comparison of crop characteristics of Ahrittaun bean, IT109098 (mother plant) and K7-2 (father plant)

| Variety | Leaf shape | Color of hypocotyl | Trichome color | Flower color | Blooming | Maturing | Stem length (cm) | Nodes of main stem | Pods per plant |
|---|---|---|---|---|---|---|---|---|---|
| Ahrittaun bean | Oval | Green | Gray | White | August 5 | October 16 | 261 | 32 | 2.3 |
| IT109098 (mother plant) | Oval | Purple | Gray | Purple | August 2 | October 25 | 214 | 27 | 2.2 |
| K7-2 (father plant) | Oval | Green | Brown | White | August 14 | October 9 | 151 | 23 | 2.7 |

TABLE 3

Comparison of crop characteristics of Ahrittaun bean, IT109098 (mother plant) and K7-2 (father plant)

| Variety | Seed characteristics | | | | Germination rate (%) | Recovery rate (%) |
|---|---|---|---|---|---|---|
| | Shape | Seed coat color | Hilum color | g per 100 pods | | |
| Ahrittaun bean | Rectangular oval | Brown | Brown | 8.8 | 82 | 17 |
| IT109098 (mother plant) | Rectangular oval | Brown | Brown | 11.1 | 100 | 0 |
| K7-2 (father plant) | Spherical | Black | Black | 5.3 | 62 | 36 |

As shown in Tables 1-3, the *Aritaunkong* of Example 1 is semi-indeterminate and has a semi-horizontal shape. The color of the hypocotyl is green, the flower color is white and the trichome color is brown.

Figure 4A:
FIG. 4A compares the color of the hypocotyl of *Aritaunkong* (left), a new soybean (*Glycine max*) variety according to an aspect of the present disclosure, with IT109098 (right) as a reference variety.
Figure 4B:
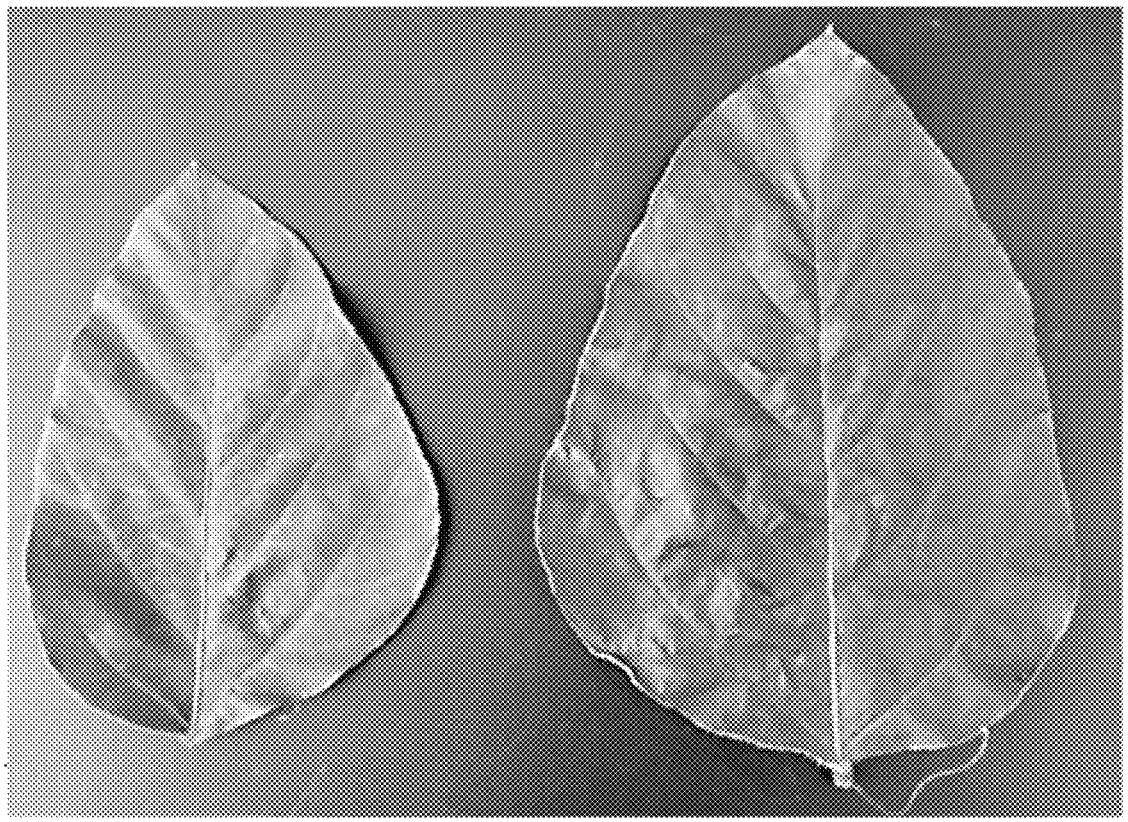
FIG. 4B compares the shape of the lateral leaflet of *Aritaunkong* (left), a new soybean (*Glycine max*) variety according to an aspect of the present disclosure, with IT109098 (right) as a reference variety.
Figure 5A:
FIGS. 5A-5C compare the color of the flower of *Aritaunkong* (FIG. 5A and left in FIG. 5C), a new soybean (*Glycine max*) variety according to an aspect of the present disclosure, with IT109098 (FIG. 5B and right in FIG. 5C) as a reference variety.

Specifically, as shown in FIG. 4A, the color of the hypocotyl of the *Aritaunkong* of Example 1 is green (left in FIG. 4A), whereas the color of the hypocotyl of the mother plant IT109098 is violet (right in FIG. 4A). In addition, as shown in FIG. 48, the length/width ratio of the lateral leaflet of the *Aritaunkong* of Example 1 (left in FIG. 4B) is smaller than that of the mother plant IT109098 (right in FIG. 4B). The flower color is compared in FIGS. 5A-5C.

Figure 5B:
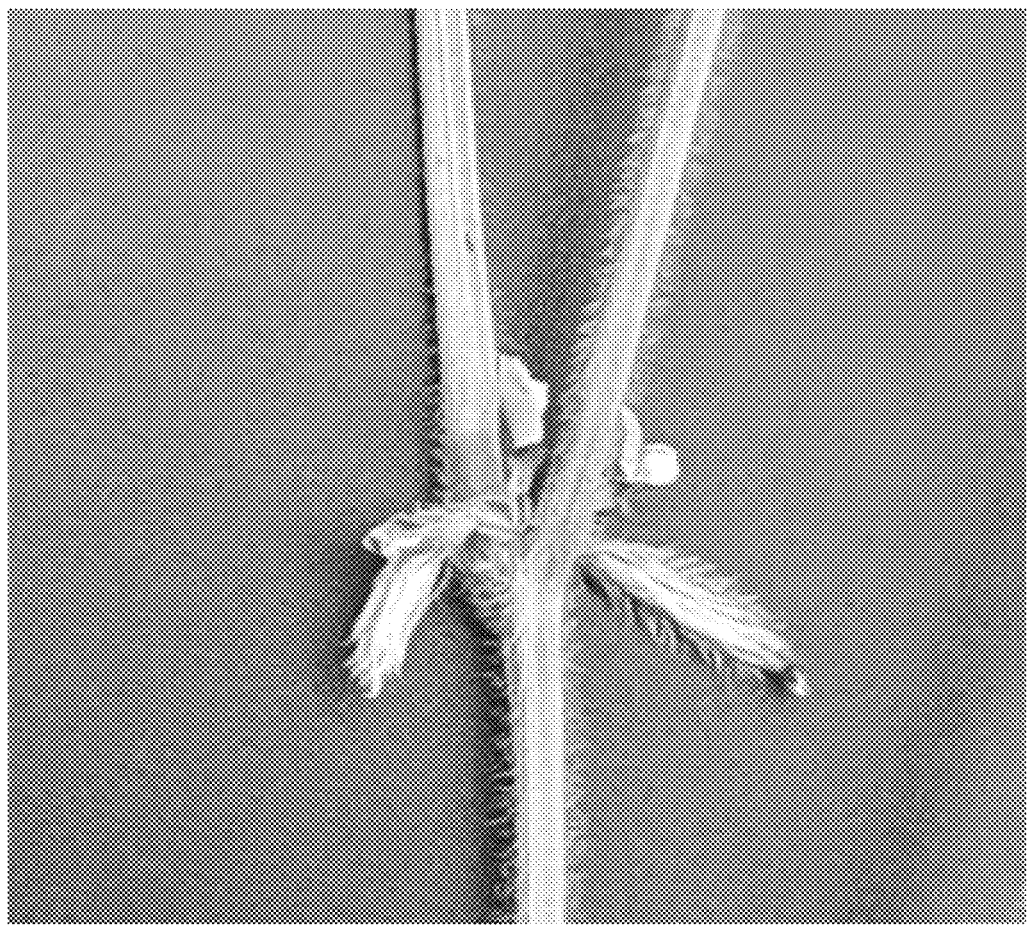
Figure 5C:
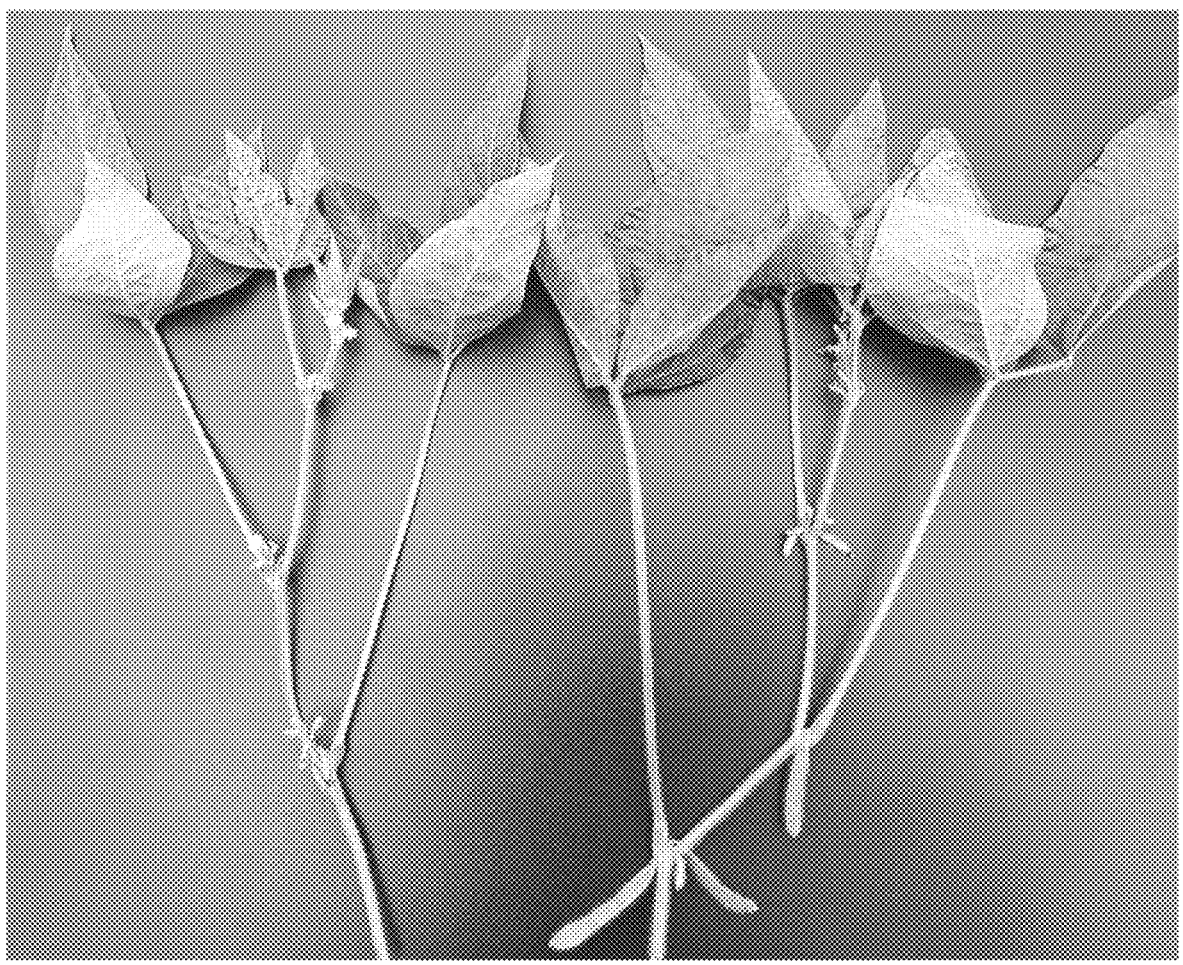
Figure 6A:
FIG. 6A shows the photograph of *Aritaunkong*, a new soybean (*Glycine max*) variety according to an aspect of the present disclosure, taken during the medium phase of cultivation.
Figure 6B:
FIG. 6B shows the photograph of IT10909, a reference variety of *Aritaunkong* which is a new soybean (*Glycine max*) variety according to an aspect of the present disclosure, taken during the medium phase of cultivation.

Whereas the flower color of the *Aritaunkong* of Example t is white (FIG. 5A), the flower color of the mother plant IT109098 is violet (FIG. 5B).

Meanwhile, whereas the *Aritaunkong* of Example 1 bloomed 3 days later than the mother plant IT109098 on August 5, it matured 9 days faster on October 16. The stem length was very long as 261 cm and the main stem had as many as 32 nodes (Table 2). Since the *Aritaunkong* of Example 1 matures very late, it is needed to be seeded by mid-June in the central and northern regions.

[Preparation Example] Preparation of Soybean Seed Extract

An extract was prepared from the seed of the *Aritaunkong* bred in Example 1 as follows.

A powder was prepared by pulverizing the seed of each of the *Aritaunkong* bred in Example 1, the mother plant IT109098 and the father plant K7-2 with a mill (Tube Mill 100 Control, IKA). After adding 100 g of the obtained soybean powder to 1 L of an 80 wt % ethanol aqueous solution, followed by extraction at room temperature (25° C.) for 24 hours, the extract was filtered through filter paper. Then, the filtered extract was dried using a vacuum concentrator to obtain each of 15.7 g (*Aritaunkong*), 16.3 g (IT109098) and 14.7 g (K7-2) of extracts.

[Test Example 1] Investigation of Antioxidant Activity

In order to investigate the antioxidant activity of the extract of the *Aritaunkong* bred in Example 1, the DPPH (1,1-diphenyl-2-picrylhydrazyl) oxidation-inhibiting effect of each soybean extract prepared in Preparation Example was compared by monitoring the change in absorbance occurring as a result of reduction of DPPH.

Specifically, after preparing 190 μL of a 100 μM (in ethanol) DPPH solution and the soybean extract of Preparation Example and the synthetic antioxidant Trolox (positive control group) to a concentration of 10,000 ppm, they were diluted to final concentrations of 500 ppm, 250 ppm, 125 ppm, 62.5 ppm, 31.25 ppm and 15.63 ppm. After preparing 10-μL reaction solutions by mixing them, absorbance was measured at 540 nm after incubation at 37° C. for 30 minutes. The analysis result is shown in Table 4. The $IC_{50}$ indicates the sample concentration when the absorbance was decreased by 50% due to the addition of the sample.

TABLE 4

| Test substance | DPPH radical-scavenging ability ($IC_{50}$) |
|---|---|
| Trolox (positive control group) | 53.2 ppm |
| Ahrittaun bean extract | 41.4 ppm |
| IT109098 (mother plant) extract | 105.9 ppm |
| K7-2 (father plant) extract | 73.4 ppm |

As can be seen from Table 4, the DPPH radical-scavenging ability ($IC_{50}$) of the extract of the *Aritaunkong* bred in Example 1 was 41.4 ppm, which was remarkably lower than those of the mother plant IT109098 (105.9 ppm) or the father plant K7-2 (73.4 ppm). In particular, the value was even lower than that of the positive control group, Trolox. Since the *Aritaunkong* exhibited superior antioxidant activity as compared to the extracts of the mother plant or the father plant, it was confirmed that a composition or functional health food, which contains the new soybean variety according to an aspect of the present disclosure or an extract thereof as an active ingredient, can protect skin from oxidative stress due to superior antioxidant effect.

[Test Example 2] Investigation of Antiaging Activity

In order to investigate the antiaging activity of the extract of the *Aritaunkong* bred in Example 1, the collagenase (MMP-1) expression-inhibiting effect of each of the soybean extracts prepared in Preparation Example was assessed.

Specifically, after placing human fibroblasts (Cascade Biologics, Portland, OR, USA) on a 96-well microtiter plate containing DMEM (Dulbecco's modified Eagle's medium) supplemented with 2.5 wt % of fetal bovine serum at 5,000 cells/well, the cells were cultured until ~90% confluency. Then, after culturing the cells in serum-free DMEM for 24 hours and treating with each of the three soybean extracts of Preparation Example or EGCG (Sigma-Aldrich) as a positive control group, dissolved in serum-free DMEM to 10 μg/mL, for 24 hours, the cell culture was collected.

Subsequently, the degree of collagenase production in the collected cell culture was measured using a collagenase measurement kit (Amersham Pharmacia, USA). First, after placing the collected cell culture on a 96-well plate on which a primary collagenase antibody is coated uniformly, antigen-antibody reaction was conducted for 3 hours in a constant-temperature bath (36° C.). 3 hours later, after adding a chromophore-conjugated secondary collagen antibody to the 96-well plate, reaction was conducted again for 15 minutes. 15 minutes later, after developing color at room temperature for 15 minutes by adding a chromogenic substance, the reaction (color development) was stopped by adding 1 M sulfuric acid. Then, the reaction solution exhibits yellow color. The degree of yellowness is dependent on the degree of reaction. The absorbance of the 96-well plate exhibiting yellow color was measured at 405 nm using an absorption spectrometer, and the inhibition of collagenase expression was calculated according to Equation 1. The collagenase expression inhibition by the groups treated with the extract and EGCG (positive control group) was compared with that of a control group (untreated group in Table 5). The result is shown in Table 5.

Collagenase expression inhibition (%)=(1−absorbance of substance-treated cell group/absorbance of control group)×100     [Equation 1]

TABLE 5

| Test substance | Collagenase expression inhibition (%) |
|---|---|
| Untreated group | 0 |
| EGCG (positive control group) | 60.8 |
| Ahrittaun bean extract | 69.6 |
| IT109098 (mother plant) extract | 50 |
| K7-2 (father plant) extract | 26.1 |

As can be seen from Table 5, the extract of the *Aritaunkong* bred in Example 1 showed collagenase expression inhibition of 69.6%, which was superior to those of the mother plant IT109098 (50%) or the father plant K7-2 (26.1%), and the collagenase expression-inhibiting effect of the *Aritaunkong* extract was even better than that of EGCG as the positive control group, which is known as an antiaging substance. Therefore, it was confirmed that a composition or functional health food containing the new soybean variety according to an aspect of the present disclosure or an extract thereof has superior antiaging effect, specifically skin antiaging effect.

[Test Example 3] Analysis of Epicatechin Content

For analysis of the epicatechin content contained in the seed of the *Aritaunkong* bred in Example 1, 5 g of the seed of each of the *Aritaunkong* bred in Example 1, the mother plant IT109098 and the father plant K7-2 was extracted with 40 mL of an 80 wt % ethanol aqueous solution in the same manner as in Preparation Example and HPLC analysis was performed for the extract.

Specifically, a Waters E2965 HPLC system and a 2998 PDA detector were used. Mightysil RP-18 (5 μm, 4.6×250 mm) (Kanto Chemical Co., Tokyo, Japan) was used as an analytical column. 99.9% water/0.1% acetic acid was used as a mobile phase solvent A, and 99.9% acetonitrile/0.1% acetic acid was used as a mobile phase solvent B. The flow rate of the solvents was set to 1 mL/min. The concentration gradient of the solvents used for separation of ingredients is given in Table 6, and the analysis result is shown in Table 7.

TABLE 6

| Time (min) | A (%) | B (%) |
|---|---|---|
| 0.0 | 95 | 5 |
| 5.0 | 95 | 5 |
| 30.0 | 70 | 30 |
| 40.0 | 5 | 95 |
| 43.0 | 5 | 95 |
| 50.0 | 95 | 5 |
| 55.0 | 95 | 5 |

TABLE 7

| | Epicatechin content (μg/g) |
|---|---|
| Ahrittaun bean | 4256.6 |
| IT109098 (mother plant) | 1099.0 |
| K7-2 (father plant) | 3425.7 |

As shown in Table 7, the epicatechin content was 4256.6 μg/g for the *Aritaunkong* bred in Example 1, 1099.0 μg/g for the mother plant IT109098, and 3425.7 μg/g for the father plant K7-2. Since the epicatechin content of *Aritaunkong* was remarkably higher than those of the mother plant or the father plant, it can be seen that a composition or functional health food containing the new soybean variety according to an aspect of the present disclosure or an extract thereof can be used as a food, cosmetic or pharmaceutical composition for antiaging and antioxidation.

Hereinafter, formulation examples of the composition according to an exemplary of the present disclosure will be described in detail. However, the present disclosure is not limited by them and other formulations are also possible.

[Formulation Example 1] Nourishing Essence

A nourishing essence was prepared by a common method according to the composition described in Table 8.

TABLE 8

| Ingredients | Contents (wt %) |
| --- | --- |
| Glycerin | 3.0 |
| Butylene glycol | 3.0 |
| Propylene glycol | 3.0 |
| Carboxyvinyl polymer | 0.1 |
| Ahrittaun bean extract of Example 1 | 1.0 |
| Beeswax | 4.0 |
| Polysorbate 60 | 1.5 |
| Caprylic/capric triglyceride | 5.0 |
| Squalane | 5.0 |
| Sorbitan sesquioleate | 1.5 |
| Cetearyl alcohol | 1.0 |
| Triethanolamine | 0.2 |
| Antiseptic and flavorant | Adequate |
| Purified water | Balance |
| Total | 100 |

[Formulation Example 2] Nourishing Lotion

A nourishing lotion was prepared by a common method according to the composition described in Table 9.

TABLE 9

| Ingredients | Contents (wt %) |
| --- | --- |
| Purified water | Balance |
| Glycerin | 3.0 |
| Butylene glycol | 3.0 |
| Liquid paraffin | 5.0 |
| β-Glucan | 7.0 |
| Carbomer | 0.1 |
| Ahrittaun bean extract of Example 1 | 1.0 |
| Caprylic/capric triglyceride | 3.0 |
| Squalane | 5.0 |
| Cetearyl glucoside | 1.5 |
| Sorbitan stearate | 0.4 |
| Polysorbate 60 | 1.5 |
| Antiseptic | Adequate |
| Flavorant | Adequate |
| Colorant | Adequate |
| Triethanolamine | 0.1 |
| Total | 100 |

[Formulation Example 3] Nourishing Cream

A nourishing cream was prepared by a common method according to the composition described in Table 10.

TABLE 10

| Ingredients | Contents (wt %) |
| --- | --- |
| Glycerin | 3.5 |
| Butylene glycol | 3.0 |
| Liquid paraffin | 7.0 |
| β-Glucan | 7.0 |
| Carbomer | 0.1 |
| Ahrittaun bean extract of Example 1 | 1.0 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |

TABLE 10-continued

| Ingredients | Contents (wt %) |
| --- | --- |
| Triethanolamine | 0.1 |
| Antiseptic and flavorant | Adequate |
| Purified water | Balance |
| Total | 100 |

[Formulation Example 4] Hair Pack

A pack was prepared by a common method according to the composition described in Table 11.

TABLE 11

| Ingredients | Contents (wt %) |
| --- | --- |
| Glycerin | 4.0 |
| Polyvinyl alcohol | 15.0 |
| Hyaluronic acid extract | 5.0 |
| β-Glucan | 7.0 |
| Allantoin | 0.1 |
| Ahrittaun bean extract of Example 1 | 1.0 |
| Nonyl phenyl ether | 0.4 |
| Polysorbate 60 | 1.2 |
| Ethanol | Adequate |
| Antiseptic and flavorant | Adequate |
| Purified water | Balance |
| Total | 100 |

[Formulation Example 5] Ointment

An ointment was prepared by a common method according to the composition described in Table 12.

TABLE 12

| Ingredients | Contents (wt %) |
| --- | --- |
| Ahrittaun bean extract of Example 1 | 2.0 |
| β-1,3-Glucan | 10.0 |
| Beeswax | 10.0 |
| Polysorbate | 5.0 |
| PEG 60 hydrogenated castor oil | 2.0 |
| Sorbitan sesquioleate | 0.5 |
| Vaseline | 5.0 |
| Liquid paraffin | 10.0 |
| Squalane | 5.0 |
| Shea butter | 3.0 |
| Caprylic/capric triglyceride | 5.0 |
| Glycerin | 10.0 |
| Propylene glycol | 10.2 |
| Triethanolamine | 0.2 |
| Antiseptic, colorant and flavorant | Adequate |
| Purified water | Balance |
| Total | 100 |

[Formulation Example 6] Preparation of Medication for Topical Application (Patch)

A medication for topical application (patch) was prepared by a common method according to the composition described in Table 13.

TABLE 13

| Ingredients | Contents (wt %) |
| --- | --- |
| Ahrittaun bean extract of Example 1 | 2.0 |
| β-1,3-Glucan | 3.0 |
| Diethylamine | 0.7 |
| Sodium sulfite | 0.1 |
| Polyoxyethylene lauryl ether (EO = 9) | 1.0 |
| Polyhydroxyethylene cetyl stearyl ether (Cetomacrogol 1000) | 1.0 |
| Viscous paraffin oil | 2.5 |
| Caprylic/capric ester (Cetiol LC) | 2.5 |
| Polyethylene glycol 400 | 3.0 |
| Polycarylic acid (Carbopol 934P) | 1.0 |
| Purified water | Balance |
| Total | 100 |

[Formulation Example 7] Preparation of Powder

*Aritaunkong* extract of Example 1 2 g

Lactose 1 g

A powder was prepared by mixing the above ingredients and filling in an airtight pouch.

[Formulation Example 8] Preparation of Tablet

| | |
| --- | --- |
| Ahrittaun bean extract of Example 1 | 100 mg |
| Cornstarch | 100 mg |
| Lactose | 100 mg |
| Magnesium stearate | 2 mg |

A tablet was prepared by a common tablet-making method after mixing the above ingredients.

[Formulation Example 9] Preparation of Capsule

| | |
| --- | --- |
| Ahrittaun bean extract of Example 1 | 100 mg |
| Cornstarch | 100 mg |
| Lactose | 100 mg |
| Magnesium stearate | 2 mg |

A capsule was prepared by mixing the above ingredients and filling in a gelatin capsule.

[Formulation Example 10] Preparation of Pill

| | |
| --- | --- |
| Ahrittaun bean extract of Example 1 | 1 g |
| Lactose | 1.5 g |
| Glycerin | 1 g |
| Xylitol | 0.5 g |

The above ingredients were mixed and prepared such that 4 g per pill was obtained according to a common method.

[Formulation Example 11] Preparation of Granule

| | |
| --- | --- |
| Ahrittaun bean extract of Example 1 | 150 g |
| Soybean extract | 50 mg |
| Glucose | 200 mg |
| Starch | 600 mg |

After mixing the above ingredients and adding 100 mg of 30% ethanol, the mixture was dried at 60° C. to form a granule. The granule was filled in a pouch.

[Formulation Example 12] Drink

After mixing 50 mg of the *Aritaunkong* extract of Example 1, 10 g of glucose, 0.6 g of citric acid and 25 g of oligosaccharide syrup and adding 300 mL of purified water, 200 mL of the mixture was filled in a bottle. Then, a drink was prepared by sterilizing at 130° C. for 4-5 seconds.

[Formulation Example 13] Caramel

A caramel was prepared by mixing 50 mg of the *Aritaunkong* extract of Example 1, 1.8 g of corn syrup, 0.5 g of skim milk, 0.5 g of soybean lecithin, 0.6 g of butter. 0.4 g of hydrogenated vegetable oil, 1.4 g of sugar, 0.58 g of margarine and 20 mg of table salt.

Deposition Number

Depository agency: Korea Research Institute of Bioscience and Biotechnology

Deposition number: KCTC14220BP

Date of deposition: 20200619

The invention claimed is:

1. A soybean variety *Aritaunkong*, wherein a seed sample of the soybean variety has been deposited under Accession No. KCTC 142201BP.

2. The soybean variety of claim 1, wherein the soybean variety is a seed.

3. The soybean variety of claim 1, wherein the soybean variety is a soybean plant or a part thereof.

4. A method for producing a soybean variety, comprising:
crossing a soybean plant; and
harvesting a soybean seed obtained from the crossing, wherein one or more of the soybean plant is the soybean variety of claim 1.

5. The method for producing a soybean variety of claim 4, which further comprises:
(a) producing a seed of a progeny plant of a subsequent generation by crossing a soybean plant that has grown from the soybean seed obtained from selfing the soybean plant or crossing with another soybean plant;
(b) producing a progeny plant of a further subsequent generation by growing the progeny plant of the subsequent generation from the seed of the progeny plant of the subsequent generation and selfing the progeny plant of the subsequent generation or crossing with a second plant; and
(c) repeating the steps (a) and (b) by using the progeny plant of the further subsequent generation of the step (b) instead of the plant that has grown from the soybean seed obtained from the crossing in the step (a), wherein the steps (a) and (b) are repeated enough to produce an inbred plant from the high-yielding new soybean variety through inbreeding.

6. The method for producing a soybean variety of claim 4, wherein the produced soybean variety is an F1 soybean seed.

7. The method for producing a soybean variety of claim 4, wherein the produced soybean variety is an F1 soybean plant produced by growing the F1 soybean seed or a part thereof.

8. The method for producing a soybean variety of claim 7, which further comprises applying plant breeding to the soybean plant or a part thereof and developing a second soybean plant through the plant breeding.

9. A method for antiaging or antioxidation, comprising administering to a subject in need of antiaging or antioxidation a composition comprising an extract of the soybean variety of claim 1.

* * * * *

UNITED STATES PATENT AND TRADEMARK OFFICE
CERTIFICATE OF CORRECTION

PATENT NO. : 12,302,841 B2
APPLICATION NO. : 17/488024
DATED : May 20, 2025
INVENTOR(S) : Young Gyu Kang et al.

It is certified that error appears in the above-identified patent and that said Letters Patent is hereby corrected as shown below:

In the Specification

In Column 4, between Line 41, "BRIEF DESCRIPTION OF DRAWINGS" and Line 43, "FIG. 1" insert the following paragraph:
-- The patent or application filed contains at least one drawing executed in color. Copies of this patent or patent application publication with color drawing(s) will be provided by the Office upon request and payment of the necessary fee. --

In Column 20, Line 2, "Bioscience and Biotechnology" should read -- Bioscience and Biotechnology (KRIBB), 181, Ipsin-gil, Jeongeup-si, Jeolllabuk-do 56212, Republic of Korea, --

In Column 19-20, TABLE 1, "Ahrittaun bean and IT109098" should read -- Aritaunkong and IT109098 --, and "Ahrittaun bean IT09098" should read -- Aritaunkong IT09098 --

In Column 21-22, TABLE 1, "Ahrittaun bean and IT109098" should read -- Aritaunkong and IT109098 --, and "Ahrittaun bean IT09098" should read -- Aritaunkong IT09098 --

In Column 23-24, TABLE 2, "Comparison of cropcharacteristics of Ahrittaun bean" should read -- Comparison of cropcharacteristics of Aritaunkong --

In Column 23-24, TABLE 2, "Ahrittaun bean Oval Green Gray White August 5 October 16 261 32 2.3" should read -- Aritaunkong Oval Green Gray White August 5 October 16 261 32 2.3 --

In Column 23-24, TABLE 3, "Ahrittaun bean Rectangular oval Brown Brown 8.8 82 17" should read -- Aritaunkong Rectangular oval Brown Brown 8.8 82 17 --

In Column 24, TABLE 4, "Ahrittaun bean extract" should read -- Aritaunkong extract --

In Column 25, TABLE 5, "Ahrittaun bean extract" should read -- Aritaunkong extract --

Signed and Sealed this
Twenty-sixth Day of August, 2025

Coke Morgan Stewart
*Acting Director of the United States Patent and Trademark Office*

CERTIFICATE OF CORRECTION (continued)
U.S. Pat. No. 12,302,841 B2

In Column 26, TABLE 7, "Ahrittaun bean" should read -- Aritaunkong --

In Column 27, TABLE 8, "Ahrittaun bean" should read -- Aritaunkong --

In Column 27, TABLE 9, "Ahrittaun bean" should read -- Aritaunkong --

In Column 27, TABLE 10, "Ahrittaun bean" should read -- Aritaunkong --

In Column 28, TABLE 11, "Ahrittaun bean" should read -- Aritaunkong --

In Column 28, TABLE 12, "Ahrittaun bean" should read -- Aritaunkong --

In Column 29, TABLE 13, "Ahrittaun bean" should read -- Aritaunkong --

In Column 29, [Formulation Example 8] Preparation of Tablet, "Ahrittaun bean" should read -- Aritaunkong --

In Column 29, [Formulation Example 9] Preparation of Capsule, "Ahrittaun bean" should read -- Aritaunkong --

In Column 29, [Formulation Example 10] Preparation of Pill, "Ahrittaun bean" should read -- Aritaunkong --

In Column 30, [Formulation Example 11] Preparation of Granule, "Ahrittaun bean" should read -- Aritaunkong --

In Column 30, Lines 31-32, "Bioscience and Biotechnology" should read -- Bioscience and Biotechnology (KRIBB), 181, Ipsin-gil, Jeongeup-si, Jeolllabuk-do 56212, Republic of Korea. --